(12) United States Patent
Kawaguchi et al.

(10) Patent No.: US 8,535,699 B2
(45) Date of Patent: Sep. 17, 2013

(54) INSECT-REPELLING RESIN COMPOSITION AND EXTENDED-RELEASE INSECT-REPELLING RESIN MOLDED PRODUCT OBTAINED THEREFROM

(75) Inventors: Shinobu Kawaguchi, Toyonaka (JP); Masayuki Tatsumi, Nishinomiya (JP); Kiyoshi Mitsui, Takatsuki (JP); Masato Mizutani, Nishinomiya (JP); Kouzi Noda, Takatsuki (JP)

(73) Assignee: Sumika Life Tech, Limited, Osaka-Shi (JP)

( * ) Notice: Subject to any disclaimer, the term of this patent is extended or adjusted under 35 U.S.C. 154(b) by 0 days.

(21) Appl. No.: 12/976,084

(22) Filed: Dec. 22, 2010

(65) Prior Publication Data

US 2011/0159064 A1 Jun. 30, 2011

(30) Foreign Application Priority Data

Dec. 24, 2009 (JP) ................. 2009-293255

(51) Int. Cl.
| | |
|---|---|
| *A01N 53/00* | (2006.01) |
| *A01N 25/34* | (2006.01) |
| *A01N 25/10* | (2006.01) |
| *C08K 5/02* | (2006.01) |
| *C08K 5/06* | (2006.01) |
| *C08K 5/07* | (2006.01) |
| *C08K 5/09* | (2006.01) |
| *C08K 5/10* | (2006.01) |
| *C08L 27/06* | (2006.01) |

(52) U.S. Cl.
USPC ............ 424/411; 524/284; 524/81; 524/568; 524/700; 524/773; 524/849; 524/851; 524/881

(58) Field of Classification Search
USPC ................ 524/881, 851, 849, 773, 700, 568, 524/284, 81; 424/411
See application file for complete search history.

(56) References Cited

U.S. PATENT DOCUMENTS

| | | | |
|---|---|---|---|
| 4,150,109 A | 4/1979 | Dick et al. | |
| 5,948,832 A * | 9/1999 | Nagamatsu et al. | 523/122 |
| 2006/0229222 A1* | 10/2006 | Muller et al. | 510/267 |
| 2011/0130430 A1* | 6/2011 | Sonneck et al. | 514/365 |

FOREIGN PATENT DOCUMENTS

| | | |
|---|---|---|
| GB | 2114442 A | 8/1983 |
| JP | 2-199148 A | 8/1990 |
| JP | 9-77908 A | 3/1997 |
| JP | 2000-319105 A | 11/2000 |
| JP | 2001-264601 A | 9/2001 |
| JP | 2001-279033 A | 10/2001 |
| JP | 2006-258892 A | 9/2006 |
| WO | WO 2009/121580 * | 10/2009 |

OTHER PUBLICATIONS

"Erucic acid" Wikipedia, XP-002632152. Retrieved on Apr. 8, 2011, from URL:http://en.wikipedia.org/wiki/Erucic_acid, pp. 1-5, Wayback Machine URL Date Mar. 5, 2004.

* cited by examiner

*Primary Examiner* — Fereydoun G Sajjadi
*Assistant Examiner* — Alma Pipic
(74) *Attorney, Agent, or Firm* — Birch, Stewart, Kolasch & Birch, LLP

(57) ABSTRACT

In order to provide a controlled-release insect-controlling resin molded product and a insect-controlling resin composition for making such a controlled-release insect-controlling resin molded product that have immediate effectiveness, residual effectiveness, and preservation stability and that are excellent in merchantability and manufacturing control, the present invention uses an insect-controlling resin composition including a polyvinyl chloride resin containing a non-vaporizable insect-controlling component and erucic acid.

17 Claims, 1 Drawing Sheet

INSECT-REPELLING RESIN COMPOSITION AND EXTENDED-RELEASE INSECT-REPELLING RESIN MOLDED PRODUCT OBTAINED THEREFROM

This Nonprovisional application claims priority under 35 U.S.C. §119(a) on Patent Application No. 2009-293255 filed in Japan on Dec. 24, 2009, the entire contents of which are hereby incorporated by reference.

FIELD OF INVENTION

The present invention relates to an insect-controlling resin composition (e.c. insect-repelling resin composition) and a controlled-release insect-controlling resin (e.c. extended-release insect-repelling resin) molded product obtained therefrom.

BACKGROUND OF THE INVENTION

Conventionally, a controlled-release insect-controlling resin molded product has been obtained by the following steps: (i) kneading a saturation dissolution amount or more of a non-vaporizable insect-controlling component into a base resin; (ii) molding the resulting melt mixture into a desired shape; and (iii) gradually bleeding a supersaturation amount of the insect-controlling component onto a surface of the resulting molded product. It should be noted here that the term "non-vaporizable insect-controlling component" collectively means non-vaporizable bioactive components, such as an insecticidal or insect control compound and an insect-controlling compound, which are effective against animal parasites such as fleas and ticks. In the following, such a non-vaporizable insect-controlling component is sometimes referred to simply as "insect-controlling component". The controlled-release insect-controlling resin molded product is widely known as an insect-controlling collar for protecting a dog, cat, etc. from fleas and ticks. The insect-controlling collar is commercially available as a hermetically-packaged product. Before use, the collar is taken out of the package and worn around the neck of the dog, cat, etc.

Such a controlled-release insect-controlling resin molded product has some manufacturing and functional problems. One of the manufacturing problems is concerned with ease of manufacturing control: Bleeding of the insect-controlling component kneaded into the base resin causes the base material surface to be sticky immediately after the molding, thus placing restrictions on time (lead time) from molding to hermetic packaging. Another manufacturing problem is associated with preservation stability: In a distribution process of the product after the hermetical packaging, the insect-controlling component bleeds in the package to cause the base material surface to be sticky by the time the package is opened. In the meantime, most important ones of the functional problems as a controlled-release insect-controlling resin molded product are problems in immediate effectiveness and residual effectiveness.

The term "immediate effectiveness" here means that it takes a short time for a controlled-release insect-controlling resin molded product to come to bring about its desired effect after it is brought into use by opening the package. The term "residual effectiveness" here means that the desired effect lasts over a long time from the start of use.

Further, the term "bleed" represents a phenomenon when a molded product retains a saturation dissolution amount (a supersaturation amount) or more of an insect-controlling component, an extra portion of the insect-controlling component (=Total Amount of Insect-controlling Component Contained in Molded Product−Saturation Dissolution Amount of Insect-controlling Component in Molded Product) moves onto a surface of the molded product.

An example of such a controlled-release insect-controlling resin molded product is disclosed in Patent Literature 1 (JP 2001-279033 A (published on Oct. 10, 2001)). Patent Literature 1 discloses: (i) a resin composition containing a polyolefin resin, an insecticidal compound, and aliphatic hydrocarbon; and (ii) a molded product made of the resin composition. Further, Patent Literature 2 (JP H9-77908 A (published on Mar. 25, 1997)) discloses: (i) a resin composition containing a base resin, an active compound such as an insecticide, and a vaporizable plasticizer; and (ii) a molded product made of the resin composition.

However, in either of the techniques disclosed in these Patent Literatures, when the base resin is a polyolefin resin such as a polyethylene resin and a polypropylene resin, the base resin is poor in flexibility. As such, these techniques are not applicable to the field of animal insect-controlling collar for animals, etc. required to be flexible.

Furthermore, even though these techniques can satisfy the aforementioned ease of manufacturing control and preservation stability to some degree, they are grossly deficient in immediate effectiveness and not necessarily satisfactory in long-term residual effectiveness, thus posing the most important functional problems as a controlled-release insect-controlling resin molded product. In fact, these techniques require such a long time as three days or more from the start of use of the product after opening until an effective amount of an insect-controlling component bleeds onto the base material surface. Moreover, after a long period of time has elapsed since the start of bleeding, a decrease in bleed amount causes a decrease in amount of the insect-controlling component on the base material surface.

In view of the above, it is conceivable to increase the amount of the insect-controlling component contained. However, even the increase merely causes a slight increase in bleed amount. It can hardly be said that such sufficient immediate effectiveness corresponding to the increase in amount of the insect-controlling component contained is obtained.

SUMMARY OF THE INVENTION

The present invention has been achieved in view of the aforementioned conventional problems, and an object of the present invention is to provide an insect-controlling resin composition and a controlled-release insect-controlling resin molded product made thereof that exhibit extremely well-balanced performance. In other words, the insect-controlling resin composition and the controlled-release insect-controlling resin molded product made thereof are excellent in immediate effectiveness and long-term residual effectiveness, which are the most important functions of a controlled-release insect-controlling resin molded product. Specifically, in the insect-controlling resin composition and the controlled-release insect-controlling resin molded product made thereof, the insect-controlling component starts bleeding immediately after the molded product is taken out of the hermetically-sealed package for use, and an effective amount of the insect-controlling component keeps on bleeding over a long period of time after the start of use. At the same time, the insect-controlling resin composition and the controlled-release insect-controlling resin molded product made thereof are excellent in manufacturing control. Specifically, the insect-controlling resin composition and the controlled-release insect-controlling resin molded product made thereof have long time (lead time) from molding to hermetic packaging and excellent preservation stability in a hermetically-sealed package.

The inventors have diligently worked on the foregoing problems to find out a superior insect-controlling resin composition which not only is easy of manufacturing control and excellent in preservation stability but also has both immediate effectiveness and long-term residual effectiveness. As a result, they came to achieve the present invention by applying a polyvinyl chloride resin as a base resin and incorporating a non-vaporizable insect-controlling component and erucic acid, which is a novel component, into the polyvinyl chloride resin.

That is, in order to attain the above-described object, an insect-controlling resin composition of the present invention includes a polyvinyl chloride resin which contains a non-vaporizable insect-controlling component and erucic acid.

In the insect-controlling resin composition of the present invention, the erucic acid is contained in 1 to 5% by weight, and in particular, by 1.2 to 3% by weight, to the insect-controlling resin composition.

In the insect-controlling resin composition of the present invention, it is preferable that the non-vaporizable insect-controlling component be a pyrethroid compound. Further, the pyrethroid compound is used together with an insect growth regulating compound.

The insect-controlling resin composition of the present invention further includes, in addition to the foregoing components, a vaporizable plasticizer.

The insect-controlling resin composition of the present invention further includes, in addition to the vaporizable plasticizer, a bleeding accelerator.

In order to attain the above-described object, a controlled-release insect-controlling resin molded product of the present invention is made by molding the insect-controlling resin composition of the present invention.

It is preferable that the controlled-release insect-controlling resin molded product of the present invention be an insect-controlling sheet, and in particular, an insect-controlling collar for a pet.

An insect-controlling method of the present invention includes the step of using a resin composition including a polyvinyl chloride resin which contains a non-vaporizable insect-controlling component and erucic acid.

In the insect-controlling method of the present invention, it is preferable that the erucic acid is contained in 1 to 5 parts by weight to 100 parts by weight of the resin composition. It is more preferable that the erucic acid is contained in 1.2 to 3 parts by weight to 100 parts by weight of the resin composition.

In the insect-controlling method of the present invention, it is preferable that the non-vaporizable insect-controlling component be a pyrethroid compound.

In the insect-controlling method of the present invention, the resin composition may further include an insect growth regulating compound as a non-vaporizable insect-controlling component. Also, the resin composition may further include a vaporizable plasticizer and, in addition to the vaporizable plasticizer, a bleeding accelerator.

Use of a resin composition of the present invention is, for a purpose of controlling an insect, to use a resin composition including a non-vaporizable insect-controlling component and erucic acid.

In the use of the resin composition of the present invention, it is preferable that the erucic acid be contained in 1 to 5 parts by weight to 100 parts by weight of the insect-controlling resin composition. It is more preferable that the erucic acid be contained in 1.2 to 3 parts by weight to 100 parts by weight of the insect-controlling resin composition.

In the use of the resin composition of the present invention, it is preferable that the non-vaporizable insect-controlling component is a pyrethroid compound.

In the use of the resin composition of the present invention, the resin composition may further include an insect growth regulating compound as a non-vaporizable insect-controlling component. Further, the resin composition may include a vaporizable plasticizer and, in addition to the vaporizable plasticizer, a bleeding accelerator.

Other objects, features, and advantages of the present invention will be fully understood from the following description. The benefits of the present invention will become apparent from the following explanation with reference to the accompanying drawings.

DESCRIPTION OF THE EMBODIMENTS

Figure 1:
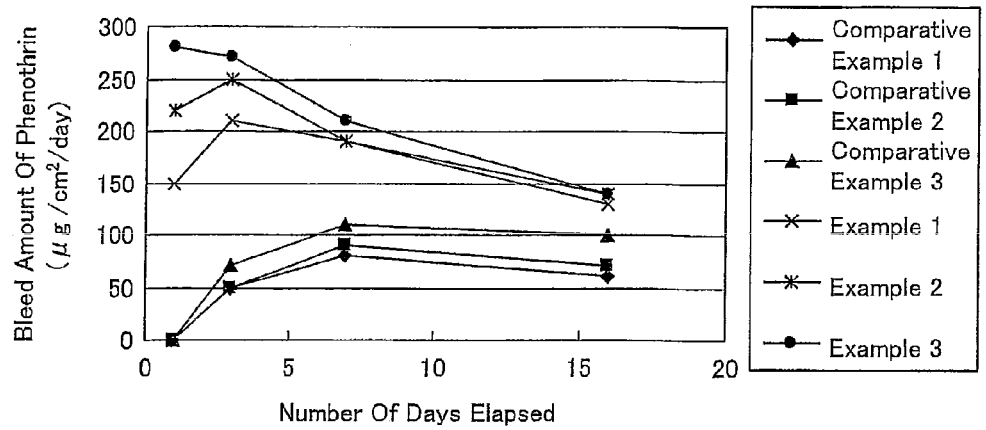
FIG. 1 is a graph showing results of "Bleed Testing—1" of molded products made of resin compositions of Comparative Examples 1 to 3 and Examples 1 to 3, respectively.

The following describes an embodiment of the present invention. Note that the present invention is not limited to the embodiment.

[1. Insect-Controlling Resin Composition]

An insect-controlling resin composition of the present invention includes a polyvinyl chloride resin containing a non-vaporizable insect-controlling component and erucic acid.

The erucic acid is straight chain fatty acid including one double bond represented by a general formula ($CH_3$—$(CH_2)_7$CH=CH$(CH_2)_{11}$COOH), and has a melting point of 33.8° C.

An amount of the erucic acid contained in the insect-controlling resin composition of the present embodiment is not particularly limited. However, too small an amount makes it difficult to obtain a desired effect, and too large an amount is economically disadvantageous. As such, for practical purposes, it is usually preferable that the insect-controlling resin composition contain 1 to 5% by weight of erucic acid. A more preferable range is between 1.2 and 3% by weight or, in consideration of preservation stability, a particularly preferable range is 1.5 to 2.8% by weight.

The polyvinyl chloride resin serves as a base resin. The polyvinyl chloride resin is satisfactory in dissolution of the non-vaporizable insect-controlling component, satisfactory in compatibility with erucic acid, and excellent in flexibility as a molded product. Due to these properties, the polyvinyl chloride resin is suitable for a controlled-release insect-controlling resin molded product to be used as an insect-controlling collar or the like.

It is preferable that the non-vaporizable insect-controlling component contained in the resin composition of the present embodiment preferably has a vapour pressure of lower than 0.01 mmHg at 20° C. or, in particular, lower than 0.001 mmHg at 20° C., for the purpose of preventing the non-vaporizable insect-controlling component from being released by vaporization during the manufacture of a molded product or by vaporization from a surface of the resulting molded product and allowing the non-vaporizable insect-controlling component to bleed onto a surface of the base material.

Such a non-vaporizable insect-controlling component is usually any of various bioactive components that are used as an insecticide or an insect repellent, as long as it is non-vaporizable. A pyrethroid compound is particularly preferably used, and examples thereof encompass pyrethrin, permethrin, allethrin, phthalthrin, prallethrin, cyphenothrin, phenothrin, resmethrin, furamethrin, imiprothrin, fenvalerate, fenpropathrin, cyhalothrin, cyfluthrin, etofenprox, tralomethrin, esbiothrin, terrarethrin, etc. Among these, phenothrin is particularly preferably used.

The non-vaporizable insect-controlling component may be used as a single compound, but may also be used together with any other non-vaporizable insect-controlling component. In particular, the non-vaporizable insect-controlling component is preferably used together with an insect growth regulator such as pyriproxyfen, bistrifluron, methoprene, hydroprene, or diflubenzuron, because the insect growth regulator further enhances the insect-controlling effect.

In addition, it is possible to use another ordinarily used synergist such as an insect-controlling component effect enhancer, e.g., piperonylbutoxide or MGK-264.

An amount of the non-vaporizable insect-controlling component contained in the insect-controlling resin composition of the present embodiment is not particularly limited, and as such, varies depending on various conditions such as the type of non-vaporizable insect-controlling component to be used, the type of polyvinyl chloride resin, the type and amount of a plasticizer to be used, and an effective period expected from a controlled-release insect-controlling resin molded product as a finished product. Considering that only a portion of the non-vaporizable insect-controlling component which has bled onto the surface of the base material serves as such an agent, it is necessary that at least a saturation dissolution amount or more of the non-vaporizable insect-controlling component be contained in the polyvinyl chloride resin serving as the base resin. If the amount contained is too small, there is a decrease in bleed amount of the effective component, and the decrease leads to deterioration in long-term insect-controlling effectiveness. On the other hand, if the amount contained is too large, there are problems such as heterogeneous mixing of the non-vaporizable insect-controlling component in the base resin and stickiness on the surface of the base material due to excessive bleeding. As such, the amount of the non-vaporizable insect-controlling component contained in the insect-controlling resin composition usually falls within a range of 10 to 40% by weight or, preferably, 15 to 30% by weight.

The insect-controlling resin composition of the present embodiment is basically constituted by incorporating the above-described non-vaporizable insect-controlling component and erucic acid into a polyvinyl chloride resin. However, it is preferable that the insect-controlling composition contains a vaporizable plasticizer and a bleeding accelerator in addition to these components. Simultaneous use of both the vaporizable plasticizer and the bleeding accelerator is particularly effective.

The vaporizable plasticizer and the bleeding accelerator are publicly known, as they are also mixed in the resin compositions disclosed in the aforementioned Patent Literatures and elsewhere. Such a publicly-known vaporizable plasticizer in the resin composition has an effect of increasing an amount of the insect-controlling component to be blended in the base resin beyond the saturation dissolution amount. On the other hand, there are problems in terms of manufacturing control: Immediately after the resin composition is molded, the vaporizable plasticizer starts vaporizing and the insect-controlling component starts bleeding onto the surface of the base material; therefore, the lead time is short and the product needs to be packaged immediately after molding.

However, if such a vaporizable plasticizer and a bleeding accelerator are used together with the erucic acid as in the present embodiment, the aforementioned advantages of the vaporizable plasticizer and the bleeding accelerator are maintained, while diminishing their defects. As a result, an insect-controlling resin composition and a molded product thereof can be obtained which are free of problems in manufacturing control and excellent in immediate effectiveness, preservation stability, and long-term residual effectiveness.

As already mentioned, such a vaporizable plasticizer is publicly known and exemplified by esters (for instance, phthalic esters, straight-chain dibasic esters, phosphoric esters, etc.) that are in a liquid state at room temperature, alcohols, ketones, animal- or plant-derived essential oil, and the like. In the present invention, it is preferable that liquid esters, in particular phthalic esters, straight-chain dibasic esters, and phosphoric esters be used. Among all, phosphoric esters such as triethyl phosphate and tributyl phosphate are preferably used.

The bleeding accelerator preferably has highest possible diffusivity in the insect-controlling resin composition, lowest possible solubility in the insect-controlling resin composition, and highest possible solubility in the vaporizable plasticizer. A particularly preferable bleeding accelerator is carboxylic acid. Specific examples of carboxylic acid are: fatty acid such as lauric acid, myristic acid, palmitic acid, and stearic acid; aromatic carboxylic acid such as benzoic acid; dicarboxylic acid such as tartaric acid, fumaric acid, and malic acid; tricaroxylic acid such as citric acid; and the like. Among these, fatty acid, or isostearic acid in particular, is preferably used.

In a case where the vaporizable plasticizer is used, an amount of the vaporizable plasticizer that is contained in the insect-controlling resin composition is usually in a range of 5 to 20% by weight.

In a case where the bleeding accelerator is used, an amount of the bleeding accelerator that is contained in the insect-controlling resin composition is usually in a range of 1 to 10% by weight.

In the present embodiment, there are no particular limitations on use of compounding agents, such as a plasticizer other than the vaporizable plasticizer and a stabilizer, which are commonly mixed into a polyvinyl chloride resin. The plasticizer, in particular, is appropriately used in order to impart desired hardness and flexibility to the intended controlled-release insect-controlling resin molded product according to its use and to improve workability.

It is preferable that such a plasticizer have a vapour pressure of lower than 0.0001 mmHg at 20° C. and low compatibility with the polyvinyl chloride resin. The plasticizer may be, for example, diisononyl adipate, di-isodecyl adipate, di-2-ethylhexyl azelate, 2-ethylhexyl sebacate, poly-2-ethylhexyl aliphatic ester, or the like. Among these, di-isodecyl adipate is preferably used.

An amount of the plasticizer that is contained in the insect-controlling composition of the present embodiment is not particularly limited, and a desired amount of the plasticizer can be appropriately contained. For example, the amount of the plasticizer that is contained in the insect-controlling composition usually falls within a range of 5 to 30% by weight.

The stabilizer is used for stably maintaining components contained in the insect-controlling resin composition and its molded product as well as the polyvinyl chloride resin serving as the base resin. Further, the stabilizer is also used for stably maintaining a shape of the molded product. A conventional stabilizer, which has been commonly used and publicly known, may be used without particular limitations. Specific examples of such conventional stabilizers encompass epoxidized soybean oil, a liquid stabilizer containing barium and zinc, barium stearate, and the like.

An amount of the stabilizer to be used is not particularly limited. The amount of the stabilizer that is contained in the insect-controlling resin composition usually falls within a range of 0.5 to 10% by weight or, preferably, 1 to 5% by weight.

Additionally, the insect-controlling resin composition may optionally contain a colorant, such as a dye or a pigment, and various compounding agents that are commonly mixed into a polyvinyl chloride resin.

The insect-controlling resin composition of the present embodiment is produced by mixing various components into the aforementioned polyvinyl chloride resin in such a manner that each of the components is contained in a desired amount. For example, the insect-controlling resin composition can be easily produced by kneading the components in the usual manner with use of a common mixer such as a Banbury mixer, a super-mixer, or an extruder.

The insect-controlling resin composition of the present invention, for example, brings about the following effects (1) to (4):

(1) During a period of time between molding of the present insect-controlling resin composition into a desired shape and hermetic packaging of the molded product, release, i.e., bleeding of the non-vaporizable insect-controlling component from the extended-release insect-controlling resin molded product at a room temperature is suppressed. This allows preservation of the molded product during the production process, thereby eliminating the need for hermetic packaging of the molded product immediately after the production. As a result, the production process can easily be controlled.

(2) Until the hermetically-packaged extended-release insect-controlling resin molded product is opened, bleeding of the non-vaporizable insect-controlling component from the controlled-release insect-controlling resin molded product is suppressed. This makes it possible, as a result, to improve preservative stability of the extended-release insect-controlling resin molded product over a long period of time.

(3) In a case where the controlled-release insect-controlling resin molded product is brought into use as an insect-controlling collar for a dog or a cat, for example, an effective amount of the insect-controlling component bleeds onto a surface of the product in a short time after the start of use. This allows the controlled-release insect-controlling molded product to bring about the intended immediate effect.

(4) After the start of use, the controlled-release insect-controlling resin molded product can keep on releasing an effective amount or more of the insect-controlling component over a long period of time. This allows the controlled-release insect-controlling molded product to bring about the intended long-term residual effect.

[2. Controlled-Release Insect-Controlling Resin Molded Product]

A controlled-release insect-controlling resin molded product of the present embodiment is obtained by molding the above-described insect-controlling resin composition of the present invention by a common resin molding processing method such as injection molding, extrusion molding, and press molding, etc. into a desired shape and size in accordance with an intended use.

The controlled-release insect-controlling resin molded product of the present embodiment can be utilized as an insect-controlling sheet, an insect-controlling screen, etc. However, because bleeding of the non-vaporizable insect-controlling component tends to be suppressed at low temperature and the insect-controlling component bleeds stably over a long period of time in an atmosphere at temperature slightly higher than room temperature, the controlled-release insect-controlling resin molded product is most effectively utilized for an animal whose body surface temperature is higher than the room temperature. In light of this, the controlled-release insect-controlling resin molded product is utilized as an ear tag for a domestic animal (a cow, for example) or an insect-controlling collar for a dog, a cat, etc. that are used in contact with a body surface of the animal. In particular, the controlled-release insect-controlling resin molded product exhibits extremely excellent performance as an insect-controlling collar that is susceptible to an animal body temperature.

The controlled-release insect-controlling resin molded product of the present embodiment may be shaped into a film, a sheet, a ring, fiber, or a net, etc. without particular limitations. The shape, size, thickness, etc. of the controlled-release insect-controlling resin molded product are appropriately selected in accordance with an intended use. For use as an insect-controlling collar, the controlled-release insect-controlling resin molded product is generally shaped into a belt or a band. For use as an ear tag, the controlled-release insect-controlling resin molded product is generally shaped into a plate.

Depending on the intended use, the controlled-release insect-controlling resin molded product may be molded into a three-dimensional shape such as a rod, a ball, or a cone.

[3. Insect-Controlling Method]

An insect-controlling method of the present embodiment includes the step of using a resin composition including a polyvinyl chloride resin which contains a non-vaporizable insect-controlling component and erucic acid.

The step of using the resin composition is not particularly limited as long as insects are controlled by placing the resin composition.

In an aspect, the resin composition can be utilized as an insect-controlling sheet, an insect-controlling screen, etc. Thus, as an aspect in which insects are controlled, the resin composition may be placed on an outer wall defining a region in which insects are to be controlled, or the region may be surrounded by an outer wall containing the resin composition. Alternatively, the resin composition may be placed in any position within the region in which insects are to be controlled. In another aspect, the resin composition is most effectively utilized for an animal. Therefore, in an aspect in which insects are controlled, the resin composition is preferably placed near an animal to be protected from insects. The resin composition may also be carried around by the animal to be protected from insects, or may be placed directly on a body surface of the animal to be protected from insects. In a case where the resin composition is carried around by the animal, the animal may wear clothes or accessories in or on which the resin composition has been placed. Alternatively, the intended animal may wear clothes or accessories containing the resin composition.

As the resin composition for use in the insect-controlling method of the present embodiment, the insect-controlling resin composition of the present invention can be used. Note that the insect-controlling composition of the present invention has already been described, and as such, it is not described here.

[4. Use of a Resin Composition]

Use of the resin composition of the present embodiment is to use, for the purpose of controlling insects, a resin composition including a polyvinyl chloride resin which contains a non-vaporizable insect-controlling component and erucic acid.

An aspect in which the resin composition is used is not particularly limited. The resin component may be directly used in the above-described insect-controlling method for controlling insects. Further, the resin component may be used in producing a product for controlling insects. For example, the aspect may be a step of incorporating the resin composition into a sheet, a screen, etc. or placing the resin composition into or onto a sheet, a screen, etc., so as to produce an insect-controlling sheet, an insect-controlling screen, etc. Alternatively, the aspect may be a step of incorporating the resin composition into an article to be placed near an animal to be protected from insects or placing the resin composition into or onto such an article. Such an article may be placed directly on a body surface of the animal, carried around by the animal, or be clothes or accessories that the animal wears.

As the resin composition for use in the present embodiment, the insect-controlling resin composition of the present invention can be used. Note that the insect-controlling resin component of the present invention has already been described, and as such, it is not described here.

Example

1. Production of Insect-Controlling Resin Compositions

<1-1. Production of Insect-Controlling Resin Compositions—1>

Among the components (A) to (J) below, the liquid components (A), (C), (D), (E), (G), (H) and the solid components (B), (F) were mixed and stirred at room temperature to give a uniformly mixed liquid. Then, the components (I) and (J) were introduced into and kneaded in a kneading machine maintained at approximately 170° C. To the components (I) and (J) being kneaded, the aforementioned mixed liquid was gradually added. The resulting mixture was further kneaded for three minutes. In this way, insect-controlling resin compositions of Comparative Examples 1 to 3 and Examples 1 to 3 as shown in Table 1 were obtained.

Note that Comparative Example 1 was prepared to be a composition having approximately the same components and mixing ratio as a commercially available insect-controlling resin molded product (i.e., to be similar to a commercial product). On the contrary, Comparative Examples 2 and 3 were each prepared to contain a larger amount of an insect-controlling component than Comparative Example 1.

(A) Phenothrin (manufactured by Sumitomo Chemical Company, Limited; marketed as Sumithrin; having a vapour pressure at 20° C. of $1.2 \times 10^{-6}$ mmHg)

(B) Pyriproxyfen (manufactured by Sumitomo Chemical Company, Limited; marketed as SumiLarv; having a vapour pressure at 20° C. of $2.2 \times 10^{-6}$ mmHg)

(C) Triethyl phosphate (having a vapour pressure at 20° C. of 0.3 mmHg)

(D) Di-isodecyl adipate (E) Isostearic acid (F) Erucic acid (manufactured by Nippon Fine Chemical Co., Ltd.)

(G) Epoxidized soybean oil (H) Liquid stabilizer containing barium and zinc (I) Barium stearate (J) Polyvinyl chloride resin (manufactured by Shin Dai-Ichi Vinyl Corporation; marketed as ZEST 1300Z)

TABLE 1

| Added Component [parts by weight] | Function | Comparative Example 1 | Comparative Example 2 | Comparative Example 3 | Example 1 | Example 2 | Example 3 |
|---|---|---|---|---|---|---|---|
| Phenothrin | Insect-controlling component | 12.0 | 14.0 | 18.0 | 18.0 | 18.0 | 18.0 |
| Pyriproxyfen | Insect-controlling component | 2.0 | 2.0 | 2.0 | 2.0 | 2.0 | 2.0 |
| Triethyl phosphate | Vaporizable plasticizer | 8.6 | 8.6 | 10.0 | 10.0 | 10.0 | 10.0 |
| Di-isodecyl adipate | Plasticizer | 24.8 | 22.8 | 17.8 | 15.8 | 15.3 | 14.8 |
| Isostearic acid | Bleeding accelerator | 2.7 | 2.7 | 2.3 | 2.3 | 2.3 | 2.3 |
| Erucic acid | Novel component | 0 | 0 | 0 | 2.0 | 2.5 | 3.0 |
| Epoxidized soybean oil | Stabilizer | 2.3 | 2.3 | 2.3 | 2.3 | 2.3 | 2.3 |
| Liquid stabilizer containing barium and zinc | Stabilizer | 1.1 | 1.1 | 1.1 | 1.1 | 1.1 | 1.1 |
| Barium stearate | Stabilizer | 0.2 | 0.2 | 0.2 | 0.2 | 0.2 | 0.2 |
| Polyvinyl chloride resin | Base material | 46.3 | 46.3 | 46.3 | 46.3 | 46.3 | 46.3 |
| | Total | 100.0 | 100.0 | 100.0 | 100.0 | 100.0 | 100.0 |

<1-2. Production of Insect-Controlling Resin Compositions—2>

Insect-controlling resin compositions of Comparative Example 4 and Example 4 were produced with the same components as shown in Comparative Example 1 and Example 1 above, so as to have the same compositions as those of Comparative Example 1 and Example 1. The insect-controlling resin compositions of Comparative Example 4 and Example 4 were produced in the following manner.

First, the liquid components (A), (C), (D), (E), (G), (H) and the solid components (B), (F) were mixed and stirred to room temperature to give a uniformly mixed liquid. Then, the components (I) and (J) were introduced into a super-mixer. To the components (I) and (J) being stirred, the mixed liquid was gradually added. At the same time, the temperature was increased up to about 130° C. The resulting mixture was then cooled off and taken out of the super-mixer. In this way, an insect-controlling resin composition (Comparative Example 4) having the same composition as Comparative Example 1 and an insect-controlling resin composition (Example 4) having the same composition as Example 1 were obtained.

2. Production of Controlled-Release Insect-Controlling Resin Molded Products

<2-1. Production of Controlled-Release Insect-Controlling Resin Molded Products—1>

The insect-controlling resin compositions of Comparative Examples 1 to 3 and Examples 1 to 3 were each pressed at a pressure of 100 kg/cm² for one minute by use of a pressing machine heated to 180° C. and then cooled off for two minutes. In this way, sheets were obtained each of which had a length of 15 cm, a width of 15 cm, and a thickness of 0.3 cm. Each of the sheets was then cut into belts each having a width of 1 cm. Thus, controlled-release insect-controlling resin molded products were obtained each of which had a width of 1 cm, a length of 15 cm, and a thickness of 0.3 cm. Each of the controlled-release insect-controlling resin molded products had a surface area of 39.6 cm².

The controlled-release insect-controlling resin molded products thus obtained were used in <3. Lead Time Testing>, <4. Preservation Testing>, and <5. Bleed Testing—1>, which will be described later.

<2-2. Production of Controlled-Release Insect-Controlling Resin Molded Products—2>

The insect-controlling resin compositions of Comparative Example 4 and Example 4 were each introduced into an extrusion molding machine heated to 140 to 150° C., extruded and molded into a belt-like molded product having a width of 1 cm and a thickness of 0.3 cm, cooled off by cooling water, and cut into a predetermined length. In this way, controlled-release insect-controlling resin molded products (collars) were obtained each of which had a width of 1 cm, a length of 35 cm, and a thickness of 0.3 cm. Note that each of the collars had a surface area of 91.6 cm².

The collars thus obtained were used in <6. Bleed Testing—2>, which will be described later.

3. Lead Time Testing

The controlled-release insect-controlling resin molded products, made of insect-controlling resin compositions of Comparative Examples 1 to 3 and Examples 1 to 3 respectively, were left in an open room at 22 to 25° C. (which correspond to room temperature), and an amount of time (lead time) it takes for stickiness to start to be seen on a surface of each of the controlled-release insect-controlling resin molded product by the naked eye was measured. If the stickiness is seen on the surface, it means that "bleeding" has begun, i.e., that the insect-controlling component is released from the controlled-release insect-controlling resin molded product. This "Lead Time Testing" allows determination of a permissible period of time between the production of the molded product and hermetic packaging and, therefore, evaluation of ease of production management.

4. Preservation Testing

The controlled-release insect-controlling resin molded products, made of the insect-controlling resin compositions of Comparative Examples 1 to 3 and Examples 1 to 3 respectively, were each put in a transparent resin bag (a polyvinyl alcohol resin bag manufactured by Kaito Chemical Industry Co., Ltd.) with a chemical impermeability and then hermetically sealed. The transparent resin bags were preserved for one month in an incubator kept at 60° C. After that, the controlled-release insect-controlling resin molded products were checked by the naked eye for surface stickiness. This "Preservation Testing" allows evaluation of preservability of the controlled-release insect-controlling resin molded products in a hermetically-sealed state.

5. Bleed Testing—1

The controlled-release insect-controlling resin molded products, made of the insect-controlling resin compositions of Comparative Examples 1 to 3 and Examples 1 to 3 respectively, were left for sixteen days in an incubator kept at 35° C. (which corresponds to body temperatures of various animals such as a dog, a cat, etc.) under open condition. Changes in bleed amount of phenothrin over time were measured by wiping off a surface of each of the molded products. Specifically, the amount of phenothrin contained in a component that had bled onto the surface of the controlled-release insect-controlling molded product was measured by liquid chromatography after wiping off the surface with paper (manufactured by Nippon Paper Crecia Co., Ltd; marketed as Kimwipe) and extracting the component with acetone. In the "Bleed Testing—1", an amount of the insect-controlling component emitted from each of the controlled-release insect-controlling resin molded products was measured in a pseudo environment of actual use. This allows evaluation of immediate effectiveness of the controlled-release insect-controlling resin molded product in actual use.

6. Bleed Testing—2

The controlled-release insect-controlling resin molded products (collars), made of the insect-controlling resin compositions of Comparative Example 4 and Example 4 respectively, were left for four months in an incubator kept at 35° C. (which corresponds to body temperatures of various animals such as a dog, a cat, etc.) under open condition. Changes in bleed amounts of phenothrin and pyriproxyfen over time were measured by wiping off a surface of each of the controlled-release insect-controlling resin molded products (collars). Specifically, the amounts of phenothrin and pyriproxyfen contained in a component that had bled onto the surface of the collars were measured by liquid chromatography after wiping off the surface with paper (manufactured by Nippon Paper Crecia Co., Ltd; marketed as Kimwipe) and extracting the component with acetone. In the "Bleed Testing—2", an amount of the insect-controlling components emitted from each of the controlled-release insect-controlling resin molded products (collars) was measured in a pseudo environment of actual use. This allows evaluation of immediate effectiveness and residual effectiveness of the controlled-release insect-controlling resin molded products (collars) in actual use.

7. Test Results

<Results of the Lead Time Testing>

Table 2 shows results of the "Lead Time Testing" of the controlled-release insect-controlling resin molded products produced with the insect-controlling resin compositions of Comparative Examples 1 to 3 and Examples 1 to 3, respectively.

TABLE 2

| Sample | Comparative Example 1 | Comparative Example 2 | Comparative Example 3 | Example 1 | Example 2 | Example 3 |
|---|---|---|---|---|---|---|
| Lead time [hr] | >40 | >40 | >40 | >40 | >40 | >40 |

Table 2 shows that Comparative Examples 1 to 3 and Examples 1 to 3 each have lead time longer than forty hours, which is a rough standard for allowable lead time in terms of manufacturing control and, therefore, that the controlled-release insect-controlling resin molded products of the present invention have no trouble with manufacturing, as with the conventional products.

<Results of the Preservation Testing>

Results of the "Preservation Testing" of the controlled-release insect-controlling resin molded products, produced with the insect-controlling resin compositions of Comparative Examples 1 to 3 and Examples 1 to 3 respectively, show that there is no significant difference between (i) Comparative Examples to 3 and Examples 1 and 2, which exhibited no stickiness, and (ii) Example 3, which exhibited a slight degree of stickiness. Considering the extremely severe condition of the preservation testing where the products were preserved at 60° C. for one month, the controlled-release insect-controlling resin molded products, produced with the insect-controlling compositions of Examples 1 to 3 respectively, exhibit excellent preservation stability in a hermetically-sealed state, as with the conventional products.

<Results of the Bleed Testing—1>

Table 3 shows results of the "Bleed Testing—1" of the controlled-release insect-controlling molded products produced with the insect-controlling resin compositions of Comparative Examples 1 to 3 and Examples 1 to 3, respectively. Note that FIG. 1 is a graph based on numerical data shown in Table 3.

Examples 1 to 3 allowed sufficient amounts of phenothrin to bleed. This means that whereas Comparative Examples 1 to 3 are inferior in immediate effectiveness, Examples 1 to 3 are superior in immediate effectiveness. Moreover, even several days later, Examples 1 to 3 showed low rates of decrease in bleed amount. As such, Examples 1 to 3 are also superior in residual effectiveness.

This is clearly shown also by a comparison with Comparative Example 3, which was obtained by increasing the amount of the insect-controlling component contained in Comparative Example 1, which is similar in composition a commercial product, to the same level as in Examples 1 to 3.

<Results of the Bleed Testing—2>

Figure 2:
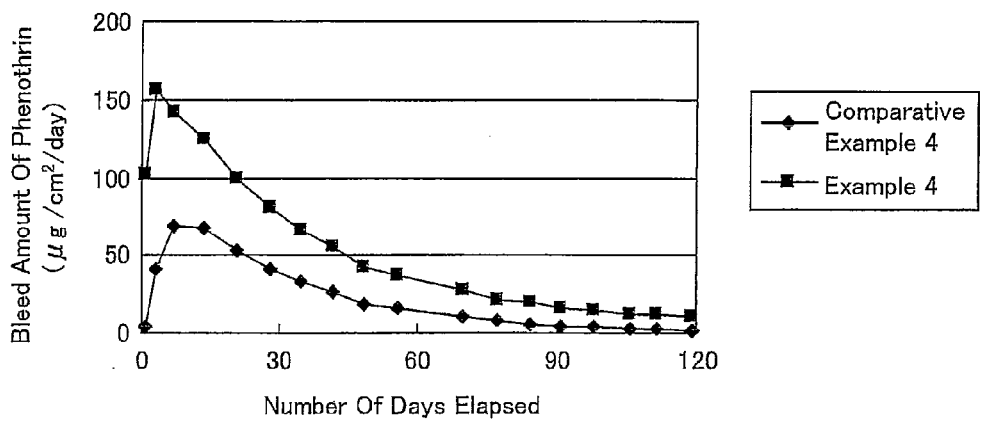
FIG. 2 is a graph showing results of "Bleed Testing—2" of collars made of resin compositions of Comparative Example 4 and Example 4, respectively.
Figure 3:
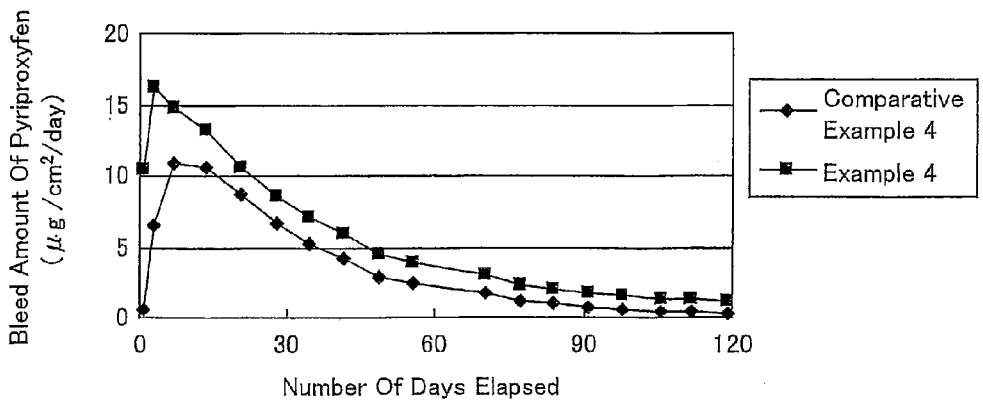
FIG. 3 is a graph showing results of "Bleed Testing—2" of collars made of resin compositions of Comparative Example 4 and Example 4, respectively.

Table 4 shows results of the "Bleed Testing—2" of the controlled-release insect-controlling molded products (collars) produced with the insect-controlling resin compositions of Comparative Example 4 and Example 4, respectively. Note that FIGS. 2 and 3 are graphs based on numerical data shown in Table 4.

TABLE 4

| | Bleed amount of phenothrin [µg/cm²/day] | | Bleed amount of pyriproxyfen [µg/cm²/day] | |
|---|---|---|---|---|
| Number of days elapsed | Comparative Example 4 | Example 4 | Comparative Example 4 | Example 4 |
| 1 | 4.0 | 101.7 | 0.6 | 10.4 |
| 3 | 41.5 | 156.5 | 6.5 | 16.2 |
| 7 | 69.3 | 141.6 | 10.9 | 14.8 |
| 14 | 67.1 | 124.4 | 10.7 | 13.1 |
| 21 | 53.4 | 98.9 | 8.6 | 10.7 |
| 28 | 41.6 | 80.2 | 6.7 | 8.6 |
| 35 | 32.8 | 66.0 | 5.2 | 7.1 |
| 42 | 26.2 | 55.3 | 4.2 | 5.9 |
| 49 | 18.4 | 41.8 | 3.0 | 4.5 |
| 56 | 15.3 | 37.0 | 2.5 | 4.0 |
| 70 | 11.1 | 28.4 | 1.8 | 3.1 |
| 77 | 7.4 | 21.7 | 1.2 | 2.3 |
| 84 | 5.9 | 19.3 | 1.0 | 2.1 |
| 91 | 4.5 | 16.1 | 0.7 | 1.7 |
| 98 | 3.6 | 14.3 | 0.6 | 1.5 |
| 106 | 2.7 | 12.4 | 0.5 | 1.3 |
| 112 | 2.5 | 11.7 | 0.4 | 1.3 |
| 119 | 1.9 | 10.4 | 0.3 | 1.1 |

According to Table 4, whereas the controlled-release insect-controlling resin molded product (collar) produced with the insect-controlling resin composition of Comparative Example 4 was small in bleed amount of the insect-controlling component even after one day and became remarkably low in bleed amount after the passage of a long period of time, the controlled-release insect-controlling resin molded product (collar) of Example 4 was large in bleed amount of the

TABLE 3

| Number of days elapsed | Bleed amount of phenothrin [µg/cm²/day] | | | | | |
|---|---|---|---|---|---|---|
| | Comparative Example 1 | Comparative Example 2 | Comparative Example 3 | Example 1 | Example 2 | Example 3 |
| 1 | 0 | 0 | 0 | 150 | 220 | 280 |
| 3 | 50 | 50 | 70 | 210 | 250 | 270 |
| 7 | 80 | 90 | 110 | 190 | 190 | 210 |
| 16 | 60 | 70 | 100 | 130 | 140 | 140 |

According to Table 3, whereas it took at least three days before Comparative Examples 1 to 3 allowed sufficient amounts of phenothrin to bleed, it took just a day before insect-controlling component from the first day. This means that the controlled-release insect-controlling resin molded product (collar) of Comparative Example 4 is inferior both in immediate effectiveness and residual effectiveness, the controlled-release insect-controlling resin molded product (collar) of Example 4 is superior in immediate effectiveness. Moreover, the controlled-release insect-controlling resin molded product (collar) of Example 4 was larger in bleed amount of the insect-controlling component than the insect-controlling resin molded product of Comparative Example 4 even after the passage of about four months. As such, the controlled-release insect-controlling resin molded product of Example 4 is superior both in immediate effectiveness and residual effectiveness.

<Evaluation Results>

These results show that: The controlled-release insect-controlling resin molded products respectively made of the insect-controlling resin components of Examples 1 to 4, which are examples of the present invention, exhibit extremely well-balanced performance of being excellent in immediate effectiveness and long-term residual effectiveness, being long in lead time, which is a standard for ease of manufacturing control, and being excellent in preservation stability; on the other hand, the insect-controlling resin molded products respectively made of the insect-controlling resin compositions of Comparative Examples 1 to 4 are high in ease of manufacturing control and preservation stability but poor in immediate effectiveness and long-term residual effectiveness, which are important functions of a controlled-release insect-controlling resin molded product during actual use.

The present invention makes it possible to provide an insect-controlling resin composition and a controlled-release insect-controlling resin molded product made thereof that exhibit extremely well-balanced performance. In other words, the insect-controlling resin composition and the controlled-release insect-controlling resin molded product made thereof are excellent in immediate effectiveness and long-term residual effectiveness, which are the most important functions of a controlled-release insect-controlling resin molded product. Specifically, in the insect-controlling resin composition and the controlled-release insect-controlling resin molded product made thereof, the insect-controlling component starts bleeding immediately after the molded product is taken out of the hermetically-sealed package for use, and an effective amount of the insect-controlling component keeps on bleeding over a long period of time after the start of use. At the same time, the insect-controlling resin composition and the controlled-release insect-controlling resin molded product made thereof are excellent in manufacturing control. Specifically, the insect-controlling resin composition and the controlled-release insect-controlling resin molded product made thereof have long time (lead time) from molding to hermetic packaging and excellent preservation stability in a hermetically-sealed package.

The present invention is applicable as a controlled-release insect-controlling resin molded product to an insect-controlling collar for a pet such as a dog, a cat, etc.; an ear tag for a domestic animal (such as a cow, sheep, etc); an insect-controlling screen; an insect-controlling sheet; and the like.

The concrete embodiments and examples discussed in the Description of Embodiments above serve solely to illustrate the technical details of the present invention, which should not be narrowly interpreted within the limits of such concrete embodiments and examples, but rather may be applied in many variations within the spirit of the present invention and the scope of the patent claims set forth below.

What is claimed is:

1. An insect-controlling resin composition comprising a polyvinyl chloride resin which contains a non-vaporizable insect-controlling component and isolated erucic acid,
   the isolated erucic acid being contained in 1.2 to 3 parts by weight to 100 parts by weight of the insect-controlling resin composition.

2. The insect-controlling resin composition according to claim 1, wherein the non-vaporizable insect-controlling component is a pyrethroid compound.

3. The insect-controlling resin composition according to claim 2, further comprising an insect growth regulating compound.

4. The insect-controlling resin composition according to claim 1, further comprising a vaporizable plasticizer.

5. The insect-controlling resin composition according to claim 4, further comprising a bleeding accelerator.

6. A controlled-release insect-controlling resin molded product made by molding the insect-controlling resin composition according to claim 1.

7. The controlled-release insect-controlling resin molded product according to claim 6, said controlled-release insect-controlling resin molded product being an insect-controlling sheet.

8. The controlled-release insect-controlling resin molded product according to claim 6, said controlled-release insect-controlling resin molded product being an insect-controlling collar for a pet.

9. An insect-controlling method comprising the step of applying to a molded product, a resin composition including a polyvinyl chloride resin which contains a non-vaporizable insect-controlling component and isolated erucic acid,
   the isolated erucic acid being contained in 1.2 to 3 parts by weight to 100 parts by weight of the resin composition.

10. The insect-controlling method according to claim 9, wherein the non-vaporizable insect-controlling component is a pyrethroid compound.

11. The insect-controlling method according to claim 10, wherein the resin composition further comprises an insect growth regulating compound.

12. The insect-controlling method according to claim 9, wherein the resin composition further comprises a vaporizable plasticizer.

13. The insect-controlling method according to claim 12, wherein the resin composition further comprises a bleeding accelerator.

14. A method for producing an insect-controlling resin composition, comprising the steps of:
   (a) mixing a non-vaporizable insect-controlling component and solid-form isolated erucic acid so as to obtain a liquid-form composition; and
   (b) mixing the liquid-form composition obtained in the step (a) with a polyvinyl chloride resin, wherein the isolated erucic acid is contained in 1.2 to 3 parts by weight to 100 parts by weight of the resin composition.

15. The method according to claim 14, wherein the non-vaporizable insect-controlling component is a pyrethroid compound.

16. An insect-controlling resin composition produced by a method as set forth in claim 14.

17. The insect-controlling resin composition according to claim 16, wherein the isolated erucic acid is contained in 1.2 to 3 parts by weight to 100 parts by weight of the insect-controlling resin composition.

* * * * *